(12) United States Patent
Tronnes

(10) Patent No.: US 8,744,595 B2
(45) Date of Patent: Jun. 3, 2014

(54) LEAD ELECTRODE MARKING SYSTEM AND METHOD FOR DEPLOYMENT

(75) Inventor: Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 393 days.

(21) Appl. No.: 12/716,426

(22) Filed: Mar. 3, 2010

(65) Prior Publication Data

US 2010/0228328 A1    Sep. 9, 2010

Related U.S. Application Data

(60) Provisional application No. 61/157,018, filed on Mar. 3, 2009.

(51) Int. Cl.
*A61N 1/05* (2006.01)

(52) U.S. Cl.
USPC .......................................... 607/115; 607/116

(58) Field of Classification Search
USPC ................................................ 607/115–120
See application file for complete search history.

(56) References Cited

U.S. PATENT DOCUMENTS

| | | | |
|---|---|---|---|
| 7,894,913 B2* | 2/2011 | Boggs et al. ................. | 607/118 |
| 8,000,805 B2* | 8/2011 | Swoyer et al. ............... | 607/117 |
| 2007/0100405 A1* | 5/2007 | Thompson et al. .......... | 607/113 |

* cited by examiner

*Primary Examiner* — Brian T Gedeon

(57) ABSTRACT

A lead includes a lead body having at least two electrodes and a lead marker. The lead marker corresponds to a size and spacing of each of the at least two electrodes. The spacing between the electrodes and lead marker corresponds to an operative length of a first lead introducer configured to be used with the lead. Lead systems that include one or more lead introducers and kits including the same are also disclosed.

3 Claims, 2 Drawing Sheets

LEAD ELECTRODE MARKING SYSTEM AND METHOD FOR DEPLOYMENT

RELATED APPLICATIONS

This application claims priority to U.S. Provisional Patent Application No. 61/157,018, filed on Mar. 3, 2009 and titled "LEAD ELECTRODE MARKING SYSTEM AND METHOD FOR DEPLOYMENT", the entire disclosure of which is incorporated herein by reference.

Lead electrodes can be made of radiopaque materials, but in some lead designs the electrodes may have minimal radiopacity, or may not be discernable from other portions of the lead under fluoroscopy or x-ray. In Interstim® therapy, available from Medtronic, Inc., test stimulation can be done with a lead that is constructed from coiled stainless steel wires. The lead includes one active electrode and the ground electrode is typically an external pad adhered to the skin of a patient being tested.

The test lead can be delivered to the patient via a needle introducer. To assist the physician in the placement of the test electrode, a mark is included on the lead body. During insertion of the lead through the needle introducer, the distal end of the mark on the lead meets the proximal end of the needle hub approximately where the distal end of the electrode is near the distal end of the needle introducer.

It is desired to offer a test stimulation lead that includes two or more electrodes on the distal end of the lead. To assist the physician in placement of the lead during the test stimulation procedure, a novel marking system and method is disclosed.

BRIEF SUMMARY

The present disclosure relates to an electrode and method of using the same in conditions where the electrodes are non-radiopaque or have minimal radiopacity or difficulty being discerned from other portions of the lead under fluoroscopy or x-ray. In particular, the present disclosure relates to a lead that includes a lead body having at least two electrodes at the distal end and a corresponding marking system on the lead body spaced away from the electrodes. The corresponding marking system includes a corresponding mark for each electrode, where each mark is the same length as the electrode to which it corresponds.

In one particular embodiment, a lead includes a lead body having at least two electrodes and a lead marker. The lead marker corresponds to the approximate size and spacing of each of the at least two electrodes. The spacing between the electrodes and lead marker corresponds to an operative length of a first lead introducer configured to be used with the lead.

In another embodiment, a lead system includes a first lead introducer configured to be used to insert a lead and having an operative length and a lead. The lead includes at least two electrodes and a lead marker corresponding to a size and spacing of each of the at least two electrodes. The spacing between the electrodes and lead marker corresponds to the operative length of the first lead introducer.

In a further embodiment, a kit includes a first lead introducer configured to be used to insert a lead and having a first operative length, a second lead introducer configured to be used to insert a lead and having a second operative length, the first operative length being less than the second operative length, and a lead extending between a distal end and a proximal end. The lead includes at least two electrodes disposed near the distal end of the lead and a first and second set of lead markers. The first set of lead markers correspond to a size and spacing of each of the at least two electrodes. The spacing between the electrodes and the first set of lead markers corresponds to the first operative length of the first lead introducer. A second set of lead markers correspond to the size and spacing of each of the at least two electrodes. The spacing between the electrodes and second set of lead markers corresponds to the second operative length of the first lead introducer. The second set of lead markers is disposed between the first set of lead markers and the proximal end of the lead.

These and various other features and advantages will be apparent from a reading of the following detailed description.

BRIEF DESCRIPTION OF THE DRAWINGS

The disclosure may be more completely understood upon consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
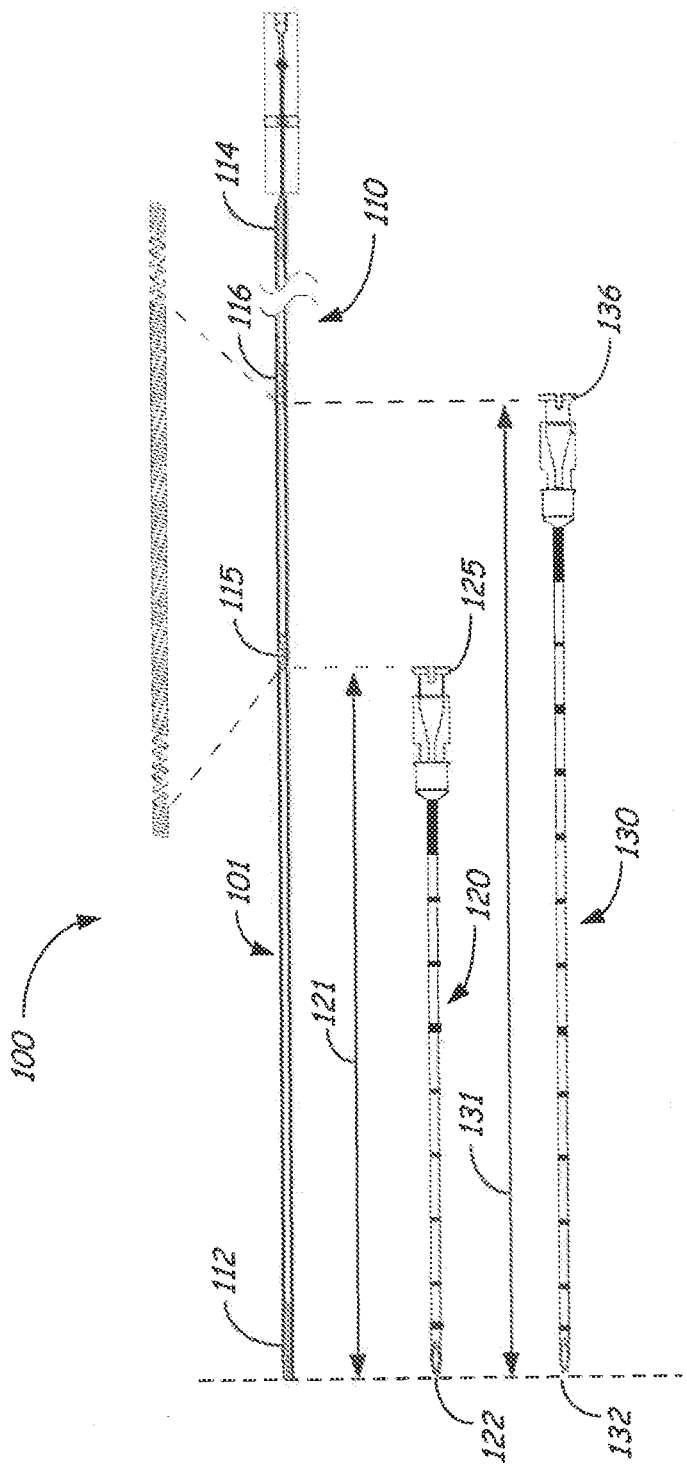
FIG. 1 is a schematic diagram of an illustrative lead system where the lead has a single active electrode.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g., 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to an electrode and method of using the same in conditions where the electrodes are non-radiopaque or have minimal radiopacity or difficulty being discerned from other portions of the lead under fluoroscopy or x-ray. In particular, the present disclosure relates to a lead that includes lead body having at least two electrodes at the distal end and a corresponding marking system on the lead body spaced away from the electrodes. The corresponding marking system includes a corresponding mark for each electrode, where each mark is the same length as the electrode to which it corresponds. The distal end of the mark is spaced from the distal end of its corresponding electrode by a length equal to the length of a needle introducer from its distal end to the proximal end of the needle hub. Additional electrodes can be included and having a similar corresponding mark. Optionally, each lead can have a set of electrodes, where there are multiple marking systems for each set of electrodes, the marking systems for each set of electrodes correspond to multiple needle introducer lengths or sizes that can be used with the test lead. Systems that include multiple introducers, each having a different length and the lead, as described above, and kits including the same are contemplated. While the present disclosure is not so limited, an appreciation of various aspects of the disclosure will be gained through a discussion of the examples provided below.

The leads, systems and kits described herein can be utilized in any useful procedure. In many embodiments, the leads, systems and kits described herein are used for stimulation in neuromodulation applications, cardiac applications or any other application delivering stimulation energy to the body.

FIG. 1 is a schematic diagram of an illustrative lead system 100 where the lead 110 has a single active electrode 112. The lead system 100 includes a lead 110 and a first introducer 120 and a second introducer 130. The first introducer 120 has a first introducer length 121 that is less than the second introducer 130 length 131. The first introducer length 121 extends between a first introducer distal end 122 to a first introducer proximal end 125.

The second introducer length 131 extends between a second introducer distal end 132 to a second introducer proximal end 136.

The lead has a lead body 101 and a single electrode 112 on a distal end of the lead 110. A ground electrode 114 is located at a proximal end of the lead 110. A lead marker 115 and 116 is located on the lead body 101 between the single electrode 112 and the ground electrode 114. The lead marker 115 and 116 is located along the length of the lead body 101 to indicate when the single electrode 112 on a distal end of the lead 110 is located at the distal end of the introducer. For example, a first lead marker 115 is located along the length of the lead body 101 to indicate when the single electrode 112 on a distal end of the lead 110 is located at the distal end 122 of the first introducer 120. Likewise, a second lead marker 116 is located along the length of the lead body 101 to indicate when the single electrode 112 on a distal end of the lead 110 is located at the distal end 132 of the second introducer 130.

Figure 2:
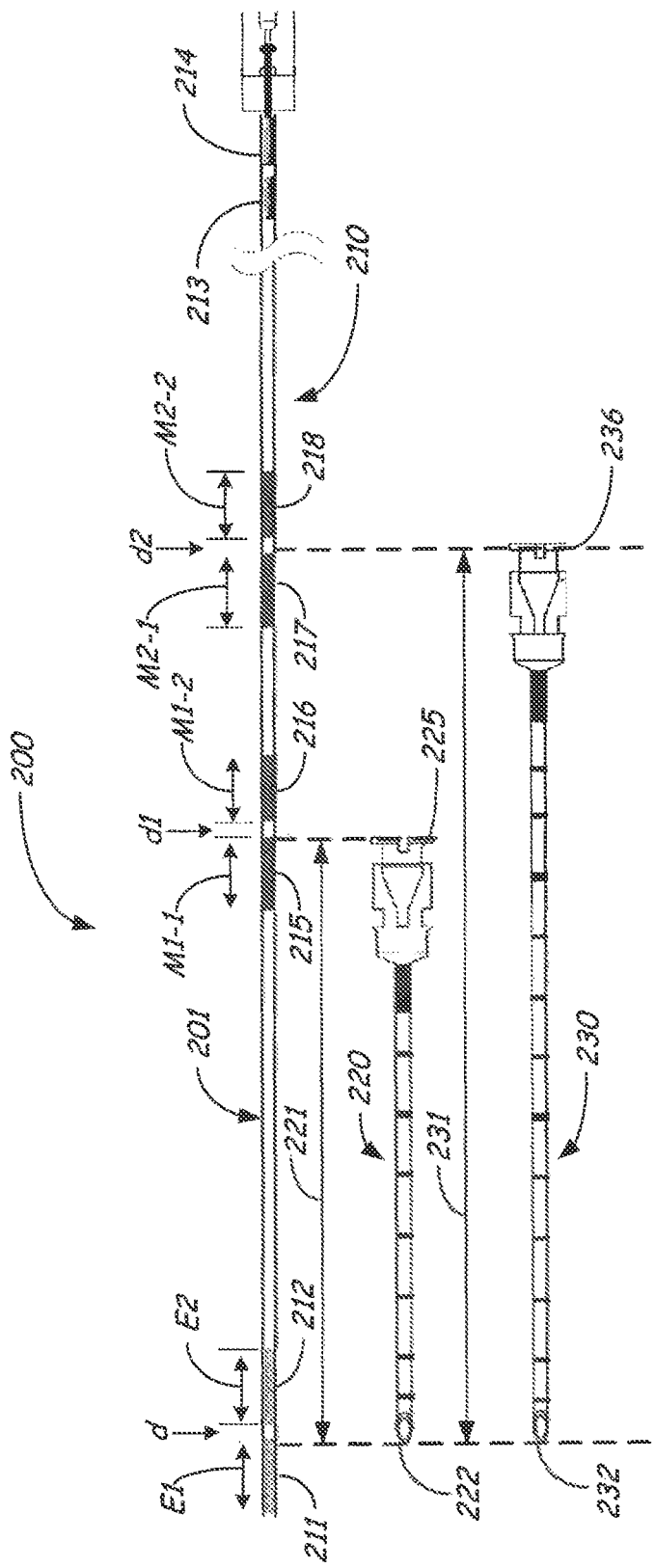
FIG. 2 is a schematic diagram of illustrative lead system where the lead has at least two active electrodes.

FIG. 2 is a schematic diagram of an exemplary lead system 200 where the lead 210 has at least two active electrodes 211, 212. The lead system 200 includes a lead 210 and a first introducer 220 and a second introducer 230. The first introducer 220 has a first introducer length 221 that is less than the second introducer 230 length 231. The first introducer length 221 extends between a first introducer distal end 222 to a first introducer proximal end 225. The second introducer length 231 extends between a second introducer distal end 232 to a second introducer proximal end 236.

The lead has a lead body 201 and a plurality of active electrodes 211, 212 on a distal end of the lead 210. Ground electrodes 213, 214 are located at a proximal end of the lead 210. The lead body 201 includes at least two sets of lead markers 215, 216 and 217, 218. The two sets of lead markers 215, 216 and 217, 218 correspond to the size and spacing of the plurality of active electrodes 211, 212 on a distal end of the lead 210. The spacing between the active electrodes 211, 212 on a distal end of the lead 210 and each set of lead markers 215, 216 and 217, 218 corresponds to a the operative length of a lead introducer 220 or 230 configured to be used to insert the lead 210.

The lead 210 illustrated, is an exemplary lead body 201 marked with indicators 215, 216 and 217, 218 that provide visualization (or a visual indication) of when the active electrodes 211, 212 on a distal end of the lead 210 are deployed into the tissue upon delivery through one or more introducers 220 or 230 of different lengths. The lead body 201 has a mark for each active electrode, each mark being equal in length to its corresponding electrode, and the marks spaced as the electrodes are spaced such that the electrode array is precisely marked along the lead body. The marking is positioned on the lead 210 relative to the length of the introducer (e.g., introduction needle), such that visual feedback is provided regarding which electrodes, and what portion of each electrode has been deployed into tissue. For purposes of convenience, the operative length of an introducer is the length from distal end of the introducer to the proximal end of the needle hub. As can be seen, where other structures are used for an introducer, the operative length will be from the most proximal end at the opening to the most distal end to which the marker can be compared upon insertion. Optionally, the hub or proximal end of the introducer may be constructed of transparent material to permit further visualization of what portion of each electrode has been deployed into tissue. Optionally, the lead may be delivered through a catheter instead of a needle, as desired.

In one illustrative embodiment, the lead 210 includes a pair of active electrodes 211 and 212, each having a particular lateral length dimension E1 and E2 (for example 10 millimeters in length) and being spaced apart by a distance d. The lead includes a first set of lead markers 215, 216 and second set of lead markers 217, 218 located on the lead body 201. The first set of lead markers 215, 216 are configured on the lead body 201 to be utilized with the first introducer 220. The second set of lead markers 217, 218 is configured on the lead body 201 to be utilized with the second introducer 220.

The first set of lead markers 215, 216 is located on the lead body 201 and spaced apart from the active electrodes 211, 212 and between the active electrodes 211, 212 and the ground electrodes 213, 214. The first set of lead markers 215, 216 has a size and spacing corresponding to the active electrode size and spacing. For example, the lead marker 215 has a length M1-1 that corresponds to the length E1 of active electrode 211 and the lead marker 216 has a length M1-2 that corresponds to the length E2 of active electrode 212, and the distance d1 between the lead markers 215 and 216 corresponds to the distance d between the active electrodes 211 and 212.

The second set of lead markers 217, 218 is located on the lead body 201 and spaced apart from the active electrodes 211, 212 and between the active electrodes 211, 212 and the ground electrodes 213, 214. The second set of lead markers 217, 218 has a size and spacing corresponding to the active electrode size and spacing. For example, the lead marker 217 has a length M2-1 that corresponds to the length E1 of active electrode 211 and the lead marker 218 has a length M2-2 that corresponds to the length E2 of active electrode 212, and the distance d2 between the lead markers 217 and 218 corresponds to the distance d between the active electrodes 211 and 212.

The distal end of each active electrode 211 and 212 is spaced apart from the distal end of its corresponding first marker (215 and 216 respectively) by a distance approximately equal to the length 221 of the first introducer 220. The length 221 being measured from its distal end 222 to the proximal end 225 of the needle hub, for example.

The distal end of each active electrode 211 and 212 is spaced apart from the distal end of its corresponding second marker (217 and 218 respectively) by a distance equal to the length 231 of the second introducer 230. The length 231 is measured from the distal end 232 to the proximal end 236 of the needle hub, for example.

The lead markers can be separate pieces from the lead body 201 or integral with the lead body 201. The lead markers can be applied to the lead body by, for example, printing, or disposing an element onto the lead body. For example, the lead markers can be shrink fit around the lead body 201 or they can be printed on the lead body 201. The particular method of how to the lead markers are placed and formed can vary based on the operation of the present disclosure.

An exemplary aspect of the present disclosure is directed to a kit including one or more introducers (e.g., needle introducers), each introducer having a length from its distal end to a proximal end of a needle hub. The kit also includes a lead body having a set of at least two electrodes, each set of electrodes having a corresponding marker, the marker duplicating the size and spacing of the electrodes, wherein the distance between the distal end of the distal electrode and the distal end of the marker is the same as the length of the introducer. If there are two or more introducers in the kit, where each introducer has a different length, then the lead body includes an equal number of markers as introducers. Optionally, there is a set of identification criteria that maps a correspondence between each introducer and the marker corresponding to a particular introducer. Optionally, each introducer uses a different color or pattern to identify its correspondence with a set of markers appropriate for use with the particular length of the introducer. For example each set of lead markers can be color coded with a different color to correspond with a color coded introducer.

An exemplary aspect of the present disclosure is directed to a method for introducing a lead body. A lead is inserted into a lead introducer. The introducer has a length from its distal end to the proximal end. The lead has at least two electrodes and a marker on the lead body. The marker includes a marking that corresponds to the size and spacing of the electrodes. The marker has a distal end that is spaced apart from the distal end of the distal electrode, the spaced apart length being the same as the length of the introducer.

Thus, exemplary embodiments of the lead electrode marking system and method for deployment are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A method for deploying an array of electrodes through an introducer and into tissue, the array comprising first and second electrodes spaced apart from one another along a distal end of a lead body, and the method comprising:
    delivering the lead body through the introducer, while viewing a first marker of a marking system that is formed at a proximal end of the lead body, the marking system to precisely mark the electrode array and including the first marker and a second marker, the first marker having a length the same as that of the first electrode of the array, the second marker having a length the same as that of the second electrode of the array, a distal end of the first marker being spaced from a distal end of the first electrode by a length that is equal to an operative length of the introducer, and the first and second markers being spaced apart from one another by a distance that is the same as a distance between the first and second electrodes;
    determining that the distal end of the first electrode of the delivered lead body is approximately aligned with a distal end of the introducer by viewing the distal end of the first marker approximately aligned with a proximal end of the introducer;
    continuing to deliver the lead body through the introducer, while continuing to view the first marker;
    determining that a proximal end of the first electrode of the delivered lead body is approximately aligned with the distal end of the introducer, and, thus, deployed, when a proximal end of the viewed first marker becomes approximately aligned with the proximal end of the introducer;
    continuing to deliver the lead body through the introducer, while viewing the second marker of the marking system;
    determining that a distal end of the second electrode of the delivered lead body is proximately aligned with the distal end of the introducer by viewing a distal end of the second marker approximately aligned with the proximal end of the introducer;
    continuing to deliver the lead body through the introducer, while continuing to view the second marker; and
    determining that a proximal end of the second electrode of the delivered lead body is approximately aligned with the distal end of the introducer, and, thus, deployed, when a proximal end of the viewed second marker becomes approximately aligned with the proximal end of the introducer.

2. The method of claim 1, wherein continuing to view each of the first and second markers comprises viewing each through a transparent hub of the introducer.

3. The method of claim 1, further comprising:
    selecting the introducer from one of a pair of introducers included in a kit before delivering the lead body through the introducer; and
    wherein the marking system further comprises a third marker and a fourth marker, the third marker being formed to have a length equal to that of the first electrode, and the fourth marker being formed to have a length equal to that of the second electrode, the length by which the distal end of the first marker is spaced from the distal end of the first electrode being equal to an operative length of the selected introducer of the pair of introducers, a distal end of the third marker of the marking system being spaced from a distal end of the first electrode by a length that is equal to an operative length of the other introducer of the pair of introducers, and the third and fourth markers being spaced apart from one another by a distance that is the same as the distance between the first and second electrodes.

* * * * *